(12) United States Patent
Cluff et al.

(10) Patent No.: US 7,742,172 B2
(45) Date of Patent: Jun. 22, 2010

(54) APPARATUS FOR VARYING THE PATH LENGTH OF A BEAM OF RADIATION

(75) Inventors: Julian A. Cluff, Cambridge (GB); Michael J. Withers, Cambridge (GB); Ian V. Bradley, Cambridge (GB)

(73) Assignee: TeraView Limited, Cambridge (GB)

( * ) Notice: Subject to any disclaimer, the term of this patent is extended or adjusted under 35 U.S.C. 154(b) by 289 days.

(21) Appl. No.: 10/528,197

(22) PCT Filed: Sep. 18, 2003

(86) PCT No.: PCT/GB03/04034

§ 371 (c)(1),
(2), (4) Date: Nov. 18, 2005

(87) PCT Pub. No.: WO2004/027491

PCT Pub. Date: Apr. 1, 2004

(65) Prior Publication Data

US 2006/0146334 A1     Jul. 6, 2006

(30) Foreign Application Priority Data

Sep. 18, 2002 (GB) .................. 0221675.2
Aug. 22, 2003 (GB) .................. 0319841.3

(51) Int. Cl.
*G01B 9/02* (2006.01)
*G01J 3/45* (2006.01)
*G02B 26/08* (2006.01)
*G02B 26/10* (2006.01)
*G02B 26/12* (2006.01)

(52) U.S. Cl. .................. 356/455; 359/213.1

(58) Field of Classification Search .................. 359/212, 359/213, 216, 211.2, 211.5, 212.1, 212.2, 359/213.1, 216.1, 218.1, 219.1; 356/455
See application file for complete search history.

(56) References Cited

U.S. PATENT DOCUMENTS 3,482,919 A * 12/1969 Barringer .................. 356/455
4,329,055 A    5/1982 Schaefer et al.
4,830,496 A * 5/1989 Young .................. 356/508
4,915,502 A * 4/1990 Brierley .................. 356/455

(Continued)

FOREIGN PATENT DOCUMENTS

DE            202 04 549 U      6/2002

(Continued)

OTHER PUBLICATIONS

J. Szydlo et al.: "Air-turbine driven optical low-coherence reflectometry at 28.6-kHz scan repetition rate," *Optics Communications*, North-Holland Publishing Co., Amsterdam, NL, vol. 154, No. 1-3, Aug. 15, 1998, pp. 1-4.

(Continued)

*Primary Examiner*—Patrick J Connolly
(74) *Attorney, Agent, or Firm*—Dickstein Shapiro LLP (57) ABSTRACT

An apparatus for varying the path length of a beam of radiation, the apparatus comprising: an element (51) rotatably mounted about an axis, said element comprising two reflective surfaces in fixed relation to one another such that radiation may be reflected between said reflective surfaces and out of the element (51); and driving means (55) for rotatably oscillating said element about said axis.

15 Claims, 8 Drawing Sheets

U.S. PATENT DOCUMENTS

| | | | |
|---|---|---|---|
| 5,150,172 A * | 9/1992 | Brierley | 356/455 |
| 5,243,404 A * | 9/1993 | Yoshikawa | 356/455 |
| 5,287,214 A * | 2/1994 | Robertson et al. | 359/260 |
| 5,394,244 A * | 2/1995 | Tsai | 356/517 |
| 5,583,638 A * | 12/1996 | Cutler | 356/455 |
| 6,144,456 A * | 11/2000 | Chavanne et al. | 356/479 |
| 6,222,632 B1 * | 4/2001 | Bakin | 356/453 |
| 2003/0072542 A1 * | 4/2003 | Furuichi et al. | 385/93 |
| 2003/0202799 A1 * | 10/2003 | Zhou et al. | 398/177 |
| 2005/0168751 A1 * | 8/2005 | Horii et al. | 356/479 |
| 2006/0146334 A1 * | 7/2006 | Cluff et al. | 356/455 |
| 2007/0091400 A1 * | 4/2007 | Dufour et al. | 359/196 |
| 2007/0091401 A1 * | 4/2007 | Dufour et al. | 359/196 |

FOREIGN PATENT DOCUMENTS

| | | |
|---|---|---|
| EP | 0 491 435 A | 6/1992 |
| EP | 1 092 943 A | 4/2001 |
| GB | 858 171 | 1/1956 |
| GB | 1 274 251 | 5/1972 |
| GB | 2 253 493 A | 9/1992 |
| JP | 4190124 A | 7/1992 |
| JP | 4295731 | 10/1992 |
| JP | 5173075 A | 7/1993 |
| JP | 9-015049 | 1/1997 |
| JP | 9-0150049 A | 1/1997 |
| JP | 2001-153605 A | 6/2001 |
| SU | 489938 | 10/1975 |
| SU | 683326 | 10/1984 |
| SU | 1423914 | 9/1988 |

OTHER PUBLICATIONS

D.M. Rife et al.: "A Compact Rotating—Mirror Autocorrelator Design for Femtosecond and Picosecond Laser Pulses," *Review of Scientific Instruments*, American Inst. Of Physics, New York, vol. 69, No. 9, Sep. 1998, pp. 3099-3102.

* cited by examiner

APPARATUS FOR VARYING THE PATH LENGTH OF A BEAM OF RADIATION

The present invention relates to the field of optics. More specifically, the present invention relates to a scanning delay line for investigative systems and particularly those that operate in the frequency range colloquially referred to as the TeraHertz frequency range. This frequency range being the range from 25 GHz to 100 THz, particularly the range from 50 GHz to 84 THz, more particularly the range from 90 GHz to 50 THz and especially the range from 100 GHz to 20 THz.

Scanning delay lines are used when it is necessary to sweep the phase of one beam of radiation with respect to another. For example, in THz imaging systems such as those described in GB 2 347 835, two beams of radiation are used: a first irradiating beam, which travels from an emitter to a detector via a sample; and a second, reference beam. In order to obtain information about the sample the phase of one of the two beams needs to be continually scanned relative to the other beam. This scanning step is achieved by providing a scanning delay line in the path of one of the beams which continuously varies the path length of one of the beams. Scanning delay lines are also used in Optical Coherence Tomography (OCT), where it is again necessary to vary the phase of one beam of radiation in a Michelson interferometer arrangement with respect to another.

Currently, there are two main types of scanning delay lines. The first of these is provided by retroreflectors which turn the beam through 180° and which are capable of linear reciprocating motion, thus extending or shortening the optical path as required.

The faster the operation of the scanning delay line, the faster the acquisition of information about the sample being investigated. It is not possible to move a retroreflector at high speeds required for applications such as imaging and thus, these types of delay lines are of limited use.

The second main type of scanning delay lines is provided by providing a constantly rotating optic within the path of one of the beams of radiation. The radiation reflects off at least one surface within the optic and thus the optical path changes as this surface rotates. These types of delay lines tend to work quicker than retroreflectors, but they suffer from the problem that they do not produce a linear variation in the phase over time and suffer from a very low duty cycle. Also, the maximum and minimum delay introduced by the scanning delay line may not be changed once with delay line has been assembled.

Modifications on the above design include work by Delachenal et al, Optics Communications 162 195-199 (1999) who use a delay line comprising a rotating polygonal mirror and a fixed glass cube and Ballif et al, Optics Letters 22, 757-759 (1997) who use a delay line comprising a rotating cube which allows internal reflection and a fixed prism.

Further attempts to solve the above problems have generally been made in relation to OCT imaging systems. Tearney et al, Optics Letters 21, 1408 to 1410 (1996) use a piezoelectric fiber stretcher to continually vary the length of the optical path of one radiation beam with respect to the other. This solution to the problems of the prior art is unlikely to be of much use in THz systems which often use pulses of radiation as such pulses will be dispersed in the optical fibers.

Rollins et al, Optics Express, 3 219-239 (1998) use a scanning delay line which comprises a single mirror and which receives light from and directs light back onto a diffraction grating. Scanning is achieved by titling the mirror under the control of a resonant scanner.

Finally, Riffe and Sabbah, Review of Scientific instruments, 69, 3099-3101 explain how a rotating prism affects the delay length of a scanning delay line in order to determine the maximum possible path length as a function of the dimensions of the prism. The prism used is a rhomboid prism and it is driven by a stepper motor.

It is an object of the present invention to at least address some of the problems of the prior art and produce a high speed scanning delay line.

In a first aspect, the present invention provides an apparatus for varying the path length of a beam of radiation, the apparatus comprising: an element rotatably mounted about an axis, said element comprising two reflective surfaces in fixed relation to one another such that radiation may be reflected between said reflective surfaces and out of the element; and driving means configured to rotatably oscillating said element about said axis.

When placed in the path of a beam of radiation, the element reflects incident radiation as it moves with respect to the beam. At certain rotation angles, the element will fail to correctly reflect the incident radiation. Radiation which is correctly reflected enters the element and is reflected by a first mirror onto a second mirror and possibly subsequent mirrors, the radiation is finally directed out of the element along a suitable radiation path which allows the beam to be directed by a further mirror or collected by an element such as a detector. Radiation which is incorrectly reflected will either fail to be reflected by the first mirror or will be reflected by the first mirror at an angle which will prevent it from being reflected by one or more of the subsequent mirrors, or it will be reflected by the mirrors within the element but will not exit the element along a suitable radiation path such that it will not be collected or re-directed by other elements in the optical circuit.

By oscillating the element as opposed to fully rotating the element, it is possible to minimise the angles, which the control element scans through, which result in incident radiation being incorrectly reflected. Thus the duty cycle of the element may be increased to values in excess of 90%. Preferably, the driving means is configured to oscillate said element through an angle of at most 40°.

The driving means preferably comprises a galvanometer. A Galvanometer comprises a coil located in a magnetic field. If a current is passed through the coil, the coil experiences a torque proportional to the current passed through the coil. Therefore, the rotation imparted by a galvanometer allows the position of the element to be finely controlled.

The galvanometer may be configured such that either rotation of the coil with respect to a fixed magnet, which generates the magnetic field, or rotation of the magnet with respect to a fixed coil is used to position the element.

Also, since the torque applied to the element via the galvanometer is dependent on the current applied to the galvanometer, the speed of the element can be varied throughout each oscillation thus allowing the element to vary the delay length, linearly with respect to time.

The element may be operated to scan linearly at a frequency of about 100 Hz. If the element is scanned sinusoidally, frequencies of 300 Hz to 400 Hz may be achieved.

Since the element is oscillated, the start and end points of the oscillation may be controlled by the driving means. Thus, the minimum and maximum points of the oscillation may be controlled by the driving means and hence, the minimum and maximum points of the scanning delay line are set by the driving means and may be altered by the driving means.

The element may be provided by two or more separate mirrors which are fixed with respect to one another. However, preferably, the element comprises a solid optic and said reflective surfaces are provided by surfaces of said optic. More preferably, said solid optic is a prism and preferably a rhomboid prism where said surfaces are two mutually parallel surfaces of said rhomboid.

If a solid optic is used, the apparatus may be operated such that internal reflection conditions are satisfied. Said reflective surfaces are preferably metallised.

Preferably, the material of the solid optic has a higher refractive index than its surroundings. For example, typically, solid optic will be mainly surrounded by air and thus a refractive index of greater than 1 is advantageous. Preferably at least 1.1, more preferably at least 1.2, even more preferably at least 1.5. By using a material with a higher refractive index, the range of angles over which radiation can be correctly reflected is increased thus allowing a large delay to be introduced by the element. Using an element with a refractive index of 1.7 allows the variation in the path length introduced by the element to be doubled over that of an element with a refractive index of 1 for certain geometries. Although the overall variation in the delay is increased, the element may still be driven to linearly vary the delay by using a galvanometer. The glass SF11 has a high refractive index.

As the element oscillates back and forth, the path of radiation exiting the element differs dependent on the rotation angle of the element. This variation in the exiting path is undesirable since radiation exiting the element will generally be collected or deflected by further optical elements. Therefore, it is preferable to keep the exiting path the same regardless of the rotation angle of the element. This may be achieved by providing a reflecting member configured to reflect radiation exiting the element back into the element, such that radiation reflected back into the element exits the element along a fixed final exit path regardless of the rotational position of the element.

Radiation which enters the element for a first time follows a first path, the reflecting member may be configured to reflect radiation back into the element such that the radiation reflected by the reflecting member follows the first path in reverse. Preferably, in order to be able to distinguish between radiation reflected back through said element and radiation which is to enter said element, the reflecting member is provided with polarisation translation means which allows the polarisation of the reflected radiation to be different to that entering the element for the first time. For example, the polarisation may be rotated by 90° or changed from being circularly polarised in one direction to being circularly polarised in the other direction. This allows the radiation to be separated by using a polarising beam splitter or the like.

Alternatively, the reflecting member may be configured to reflect radiation back into the element such that the reflected radiation follows a second path, said second path being said first path reversed and displaced along said rotation axis.

Preferably said reflecting member is a first reflecting member and the apparatus further comprises a second reflecting member, said first and second reflecting members being configured such that radiation may be reflected back through said element at least four times. In a particularly preferred arrangement radiation is passed through the element 6 times. The reflecting elements may be configured to reflect the radiation along parallel paths within the element. By reflecting radiation back through the element four or more times, the variation in the delay introduced by the element can be increased. Although the overall variation in the delay is increased, the element may still be driven to linearly vary the delay by using a galvonometer.

In a second aspect, the present invention provides a method for varying the path length of a beam of radiation, the method comprising:
providing an element comprising two reflective surfaces in fixed relation to one another such that radiation may be reflected between said reflective surfaces and out of the element;
rotatably mounting said element about an axis; and
rotatably oscillating said element about said axis.

The present invention may be used in any type of investigative or imaging system where a scanning delay line is required. For example, it may be used in OCT systems or Terahertz imaging systems or systems where analysis or identification of a sample is required.

In a third aspect, the present invention provides a system for investigating a sample, the system comprising:
an emitter for emitting radiation to irradiate said sample;
a detector for detecting radiation reflected from or transmitted by said sample, radiation travelling from the emitter to the detector following a first path;
means for supplying radiation along a second path to said detector and having a phase related to that of the radiation leaving the emitter,
the system further comprising an apparatus according to the first aspect of the invention, provided within either of the first or second paths.

In the system of the third aspect of the invention, the emitter preferably emits radiation in the THz frequency range. The system may be an imaging system or any other type of investigative system, for example a spectroscopic system.

The present invention will now be described with reference to the following non-limited preferred embodiments in which.

Figure 1A:
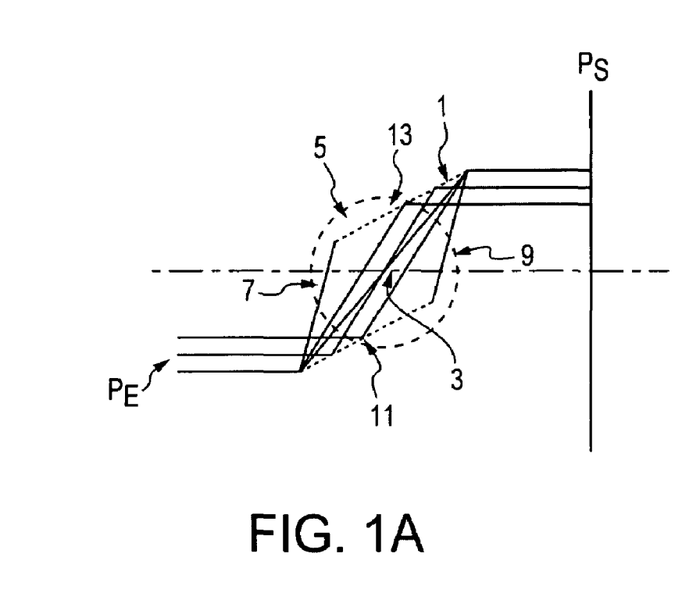
FIG. 1A schematically illustrates an apparatus in accordance with a first embodiment of the present invention in a first position and FIG. 1B schematically illustrates the apparatus of FIG. 1A in a second position.

FIG. 1A illustrates an apparatus in accordance with a first embodiment of the present invention in a first position. The apparatus comprises an element 1 which is rotatable about a central axis 3 by a rotation means 5. The rotation means 5 are only schematically shown in this diagram and will not further described in relation to this figure.

Element 1 is a rhomboid prism having two pairs of parallel planar surfaces which may be rotated through the path of a radiation beam. A first pair of parallel surfaces 7, 9 are used for entry and exit of the radiation beam from the prism 1, second pair of parallel surfaces 11, 13 are used to reflect the beam while travelling through the prism. Reflection may occur either due to the angle of the incident beam resulting in total internal reflection conditions being meet and/or surfaces 11, 13 may be metallised in order to enhance reflection.

In the example of FIG. 1A, radiation enters at the lowest part of surface 7 and is reflected from surface 11 onto reflective surface 13. Reflective surface 13 then reflects the light out through exit surface 9.

Figure 1B:
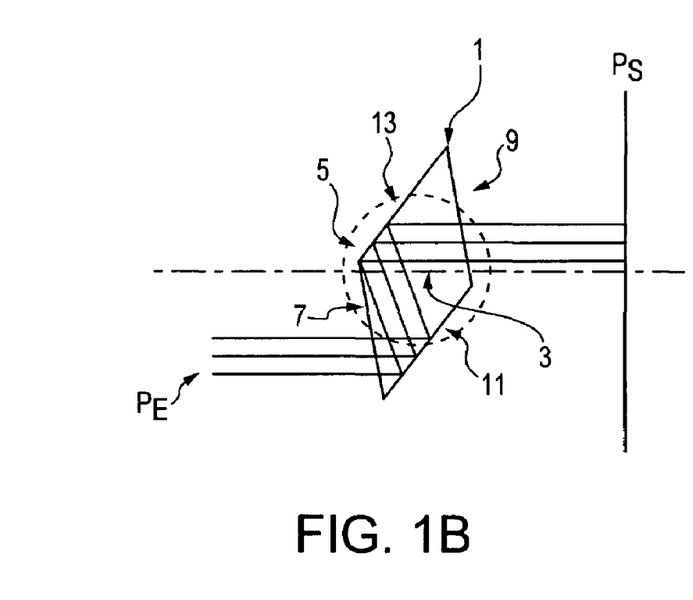

FIG. 1B illustrates the same prism as FIG. 1A but at a different rotation angle. To avoid unnecessary repetition, like reference numerals will be used to denote like features.

Due to the rotation of element 1, reflective surface 11, 13 are in a different positions in FIG. 1B to FIG. 1A.

In FIG. 1B, the different position of reflective surfaces 11, 13 causes the beam to be essentially reflected backwards whereas in FIG. 1A, the beam still travels in a generally forward direction but is deflected slightly by mirrors 11, 13. Hence, by comparing FIGS. 1A and 1B, it can be seen that the radiation path length from point Ps to point PB differs as element 1 is rotated about axis 3.

Figure 2:
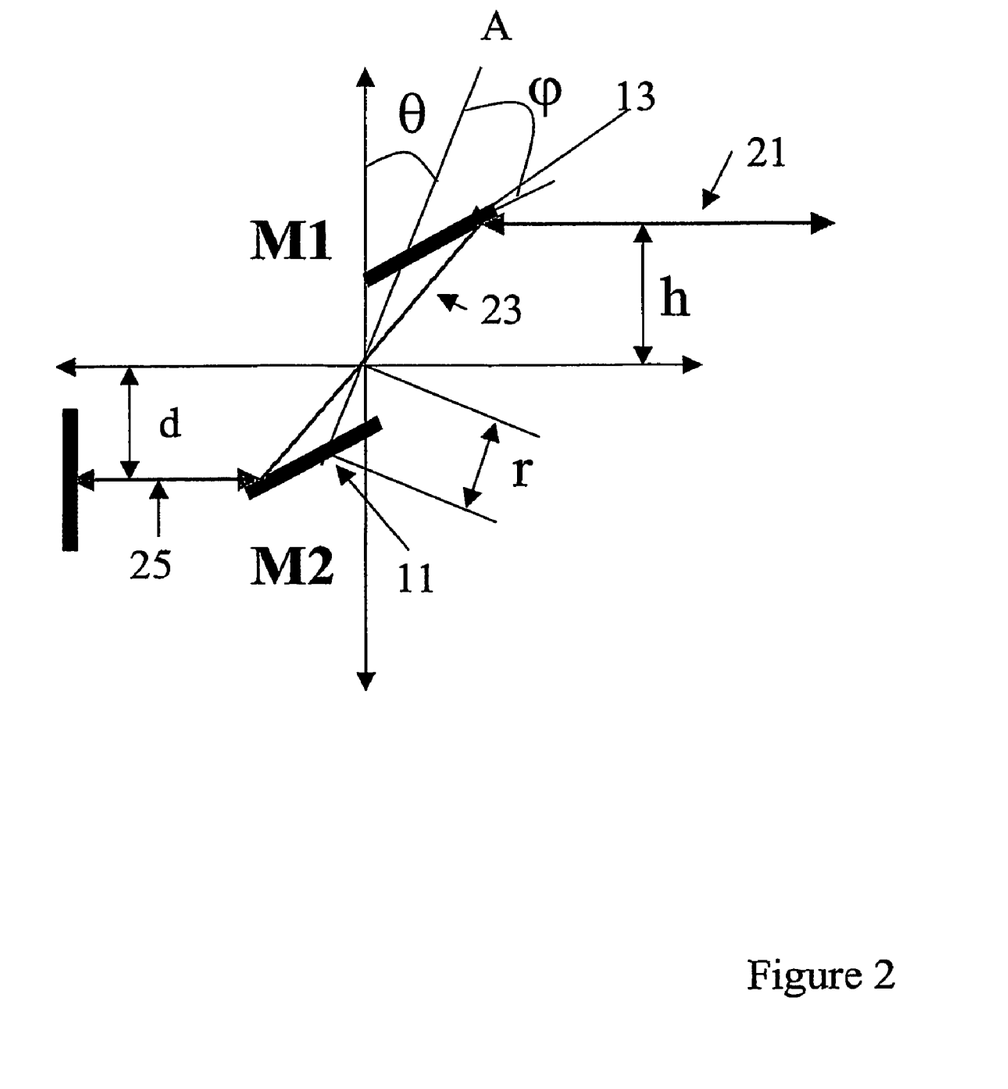
FIG. 2 is a schematic which demonstrates how the path length of radiation passing through the apparatus of FIG. 1A varies with the rotation angle of the apparatus of FIG. 1A.
Figure 3A:
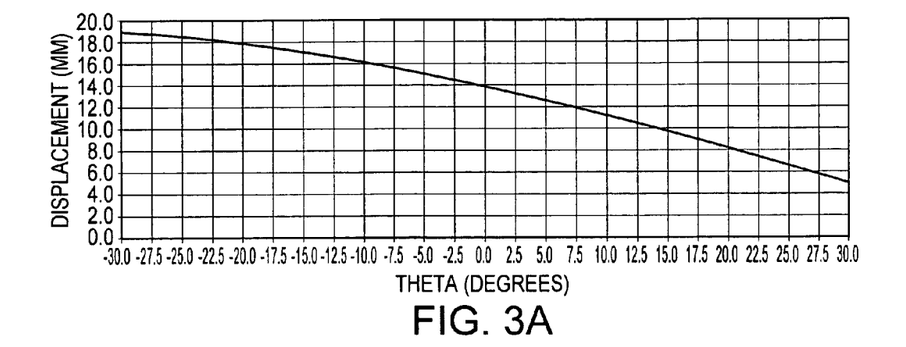
FIG. 3A is a plot of the path length in millimetres against the rotation angle θ of the apparatus of FIG. 1A.
Figure 3B:
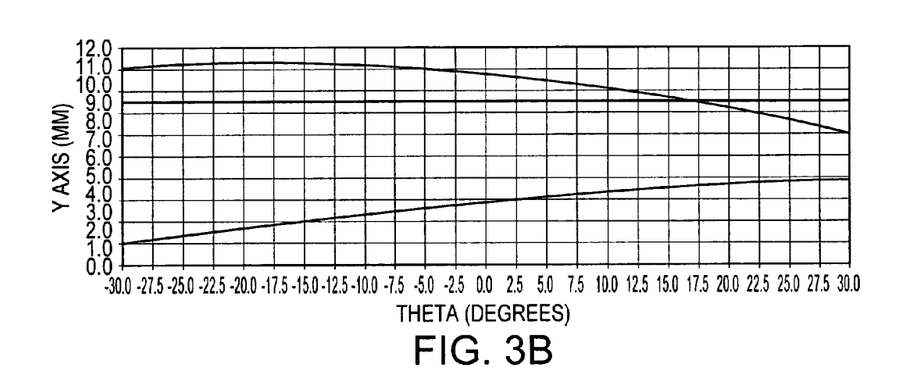
FIG. 3B is a plot of displacement along the Y-axis of the maximum height of mirror M1, the minimum height of mirror M1 and the height at which the incident radiation impinges on mirror M1 against rotation angle.
Figure 3C:
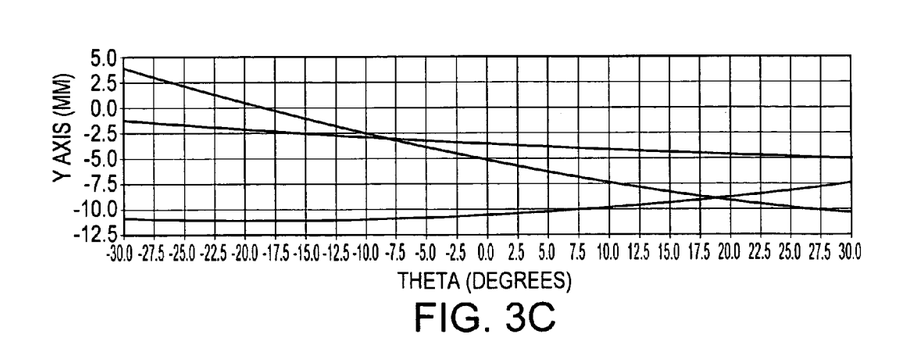
FIG. 3C is a plot of displacement along the Y-axis in millimetres of the maximum height of mirror M2, the minimum height of mirror M2 and the height of the radiation reflected from mirror M2 against the rotation angle.

How the rotation affects the path length can be seen more clearly from the graph of FIG. 2 and the results of FIG. 3.

In FIG. 2, reflective surf aces 13, 11 are renumbered as mirrors M1 and M2 respectively. The central axis A of the mirrors is rotated by angle $\theta$ about the Y-axis. Angle $\phi$ indicates the angle of the two mirrors M1 and M2 with respect to central axis A. $\theta$ represents the rotation angle of the element about the rotation axis which coincides with the origin. The diagram also illustrates the distance r which is the distance along the central axis A from the rotation axis to the centre of mirror M1 or mirror M2.

Radiation 21 enters the element at height H along the Y-axis and impinges on mirror M1. It is then reflected along path 23 to mirror M2 where it leaves the element along path 25. The positions of paths 23 and 25 will vary dependent on the rotation angle $\theta$ of the mirrors about the rotation axis, parameters h, r and $\phi$ will remain the same regardless of rotation angle $\theta$.

FIGS. 3A, 3B and 3C illustrate results where $\phi=45°$, r=7 mm, h=9 mm and the length of the mirrors is 10 mm.

FIG. 3A illustrates displacement along the Y-axis in millimetres against $\theta$ along the X-axis in degrees. The displacement corresponds to the increase or decrease of the path. When $\theta=0$, i.e. the central axis A aligns with the Y-axis, the length of the path which the radiation takes along paths 21, 23 and 25 is 14 mm. As the element 1 is rotated anti-clockwise, this path length increases due to the radiation being reflected back on itself. Approximately 5 mm is added to the path length when $\theta$ is turned through 30° anti-clockwise. Similarly as element 1 is rotated clockwise, the path length decreases and at 30° the path length is found to decrease to about 5 mm.

FIG. 3B illustrates three plots. The central fixed line at 9 mm corresponds to the height h where the radiation first impinges on mirror M1. The upper most curve corresponds to the maximum height of the surface of mirror M1 above the X axis. The lower most curve corresponds to the minimum height of mirror M1 from the X axis.

In order for radiation entering the prism to impinge on first mirrored surface M1, it is important that the height of the incident radiation is between the maximum mirror height and the minimum mirror height. It can be seen that this situation is not true for $\theta$ is excess of 17.5°. Here, the maximum height of mirror M1 falls below the height of the incident radiation, therefore, the incident radiation will just simply bypass the prism and would not be reflected.

FIG. 3C illustrates information about second mirror M2. The trace which is in the middle when $\theta=-30°$ corresponds to the maximum height of the mirror measured below the X axis of FIG. 2 and the lowest trace at $\theta=30°$ corresponds to the minimum height of mirror M2 below the X axis. The upper most trace of $\theta=30°$ corresponds to the distance d along the Y-axis which corresponds to the distance d from the X axis of FIG. 2 at which the beam leaves the element along path 25. In order for the beam to be reflected from mirror M2, this height must fall between the maximum and minimum heights of mirror M2.

It can be seen from FIG. 3C that this condition is only satisfied for the small range of angles between $\theta=-7.5°$ and $\theta=20°$. Therefore, comparing the results from FIGS. 3B and 3C, it can be seen that the prism is only effective between the angles $\theta=-7.5°$ and $\theta=17.5°$ for the specific dimensions given above. Please note, that these figures may change dependent on the angle of mirrors M1 and M2 to central axis A and the radius r of mirrors M1 and M2.

Thus, to obtain maximum efficiency from the element configured as above, it is only necessary to rotate the element through 30°.

Changing the length of the mirrors will also affect the above graphs as the length of the mirrors will affect the maximum and minimum heights of the mirrors plotted in FIGS. 3A and 3B. Extending the mirrors will decrease the minimum heights and increase the maximum heights and is therefore initially desirable. However, if the mirror lengths are increased, the top mirror M1 of FIG. 2 may occlude the lower mirror M2 thus preventing the incident beam from entering the element.

Figure 4:
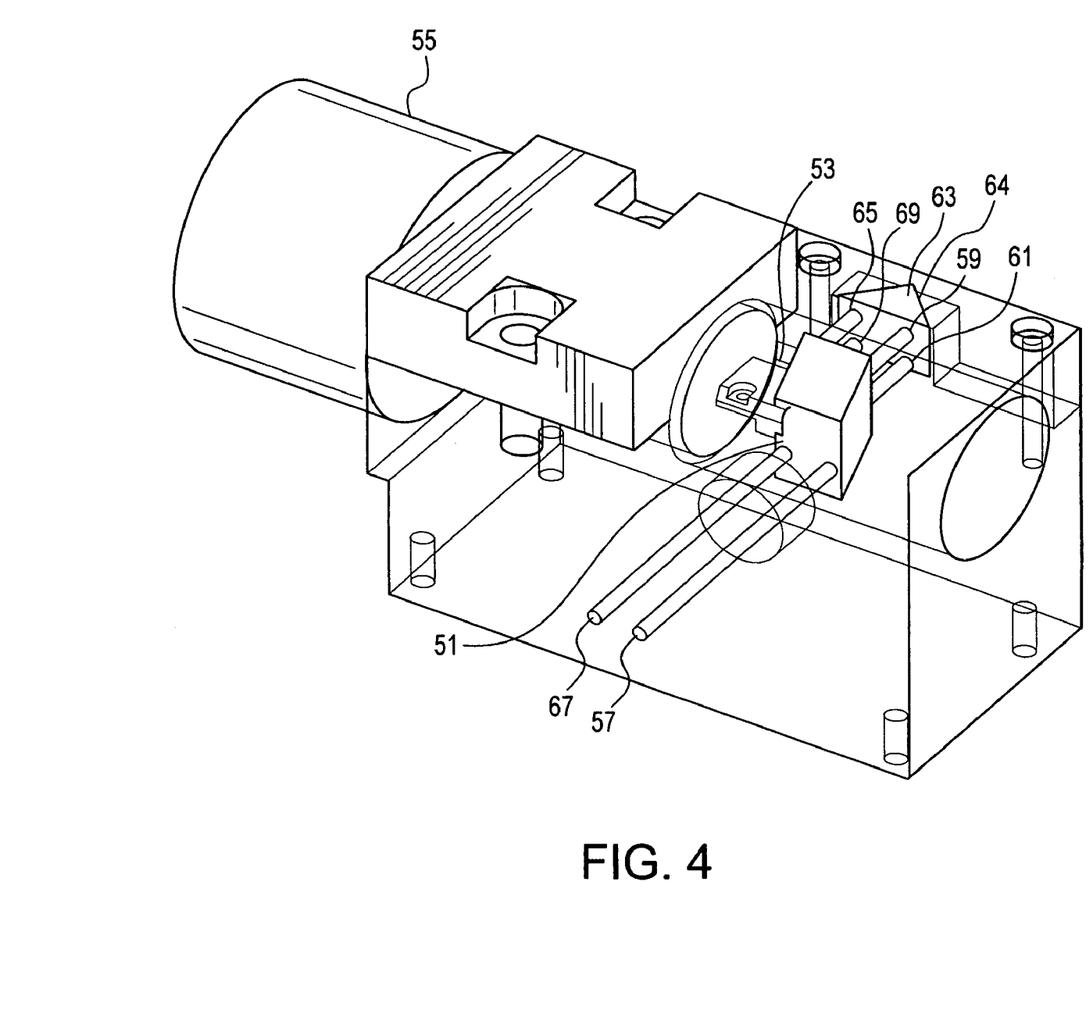
FIG. 4 is a schematic of an apparatus in accordance with a further embodiment of the present invention.

FIG. 4 illustrates an apparatus in accordance with a further embodiment of the present invention.

Rhomboid prism 51 is provided to reflect radiation. Rhomboid prism 51 is mounted upon rotational control arm 53 which is in turn controlled by galvanometer 55. By energising galvanometer 55, the control arm can be rotated back and forth such that prism 51 oscillates back and forth about its rotation axis.

Galvanometer 55 comprises a coil located in a magnetic field. If a current is passed through the coil, the coil experiences a torque proportional to the current passed through the coil. Therefore, the rotation imparted by a galvanometer allows the position of the element to be finely controlled.

Also, since the torque applied to the element via the galvanometer is dependent on the current applied to the galvanometer, the speed of the element can be varied throughout each oscillation thus allowing the element to vary the delay length linearly with respect to time.

Radiation enters the device through radiation path 57 and is reflected through prism 51 following a first radiation path and out along either exit path 59 or 61 depending on the position of the prism 51. In the figure, exit path 59 illustrates the position of the exit beam when the prism is positioned such that the beam experiences the maximum delay and exit path 61 illustrates the position of the exit beam when the prism if positioned such that the beam experiences the minimum delay.

When the beam experiences the maximum delay and exits via exit path 59, it impinges on roof prism 63 which is a right angled prism. Roof prism 63 reflects radiation beam 59 through 180° and along path 65 which is parallel to exit path 59 and displaced from path 59 in the direction of the rotation axis of the prism 51. Preferably, roof prism 63 includes polarisation translation means 64, as described above, to allow the polarisation of the reflected radiation beam (e.g., on path 65) to be different than the polarisation of the beam entering the element for the first time (e.g., beam 59).

Radiation 65 which is reflected from roof prism 63 enters prism 51 and is internally reflected by the surfaces identified in relation to FIGS. 1A, 1B and 2 following a second radiation path, and exits the prism 51 along radiation path 67.

Similarly, when the beam experiences the minimum delay and exits via exit path 61, it impinges on roof prism 63 and is reflected through 180° and along path 69. Exit path 69 is parallel to exit path 61 and displaced from path 61 in the direction of the rotation axis of the element 51.

Radiation 69 which is reflected from roof prism 63 enters prism 51 and is internally reflected by the surfaces identified in relation to FIGS. 1A, 1B and 2 following a second radiation path and exits the prism 51 along radiation path 67.

Regardless of the rotation position of the prism 51, the second radiation path is the first radiation path reversed and displaced along the rotation axis. Thus, radiation always exits the prism along final exit path 67 which is parallel to path 57 and at a fixed displacement therefrom. Hence, the scanning delay line may be easily incorporated into any optical system since its beam exit path remains fixed regardless of the delay introduced by the oscillating prism 51.

Although not shown here, in use, the galvanometer 55, control arm 53 and prism 51 will be provided on a stepper motor to adjust prism 51 to the correct position for the system.

Figure 5:
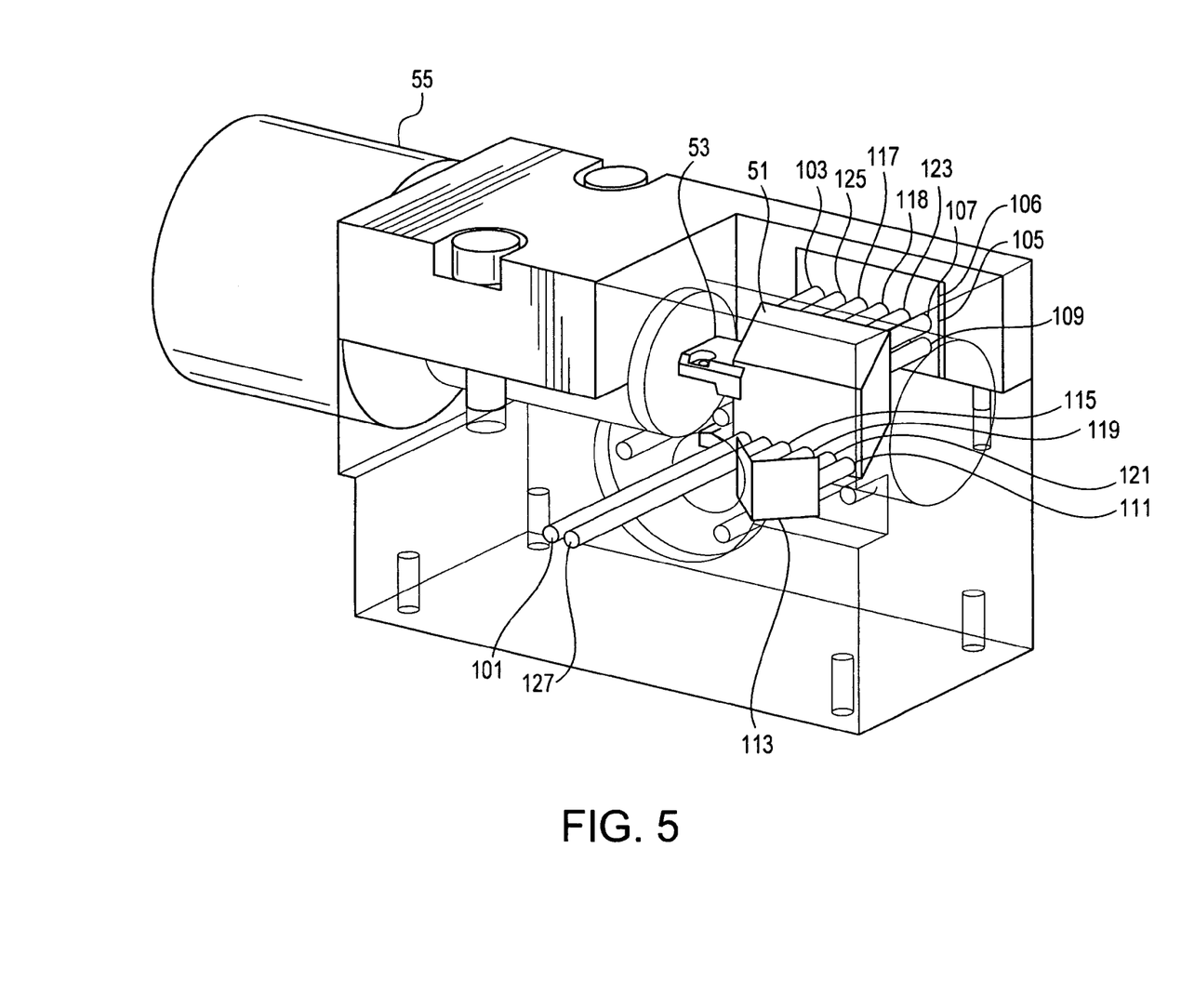
FIG. 5 is a schematic of an apparatus in accordance with a further embodiment of the present invention.

FIG. 5 schematically illustrates a variation on the apparatus of FIG. 4. To avoid unnecessary repetition, like reference numerals will be used to denote like features.

FIG. 5 primarily differs from FIG. 4 in that the beams are configured to pass through prism 51 six times.

Radiation enters the prism 51 through radiation path 101 and is reflected through prism 51 following a first radiation path and out along exit path 103. The vertical position of exit path 103 varies depending on the rotation angle of prism 51. In the figure, exit path 103 illustrates the position of the exit beam when the prism 51 is positioned such that the beam experiences the maximum delay.

When the beam experiences the maximum delay and exits via exit path 103, it impinges on large roof prism 105 which is a right angled prism. Roof prism 105 reflects radiation beam 103 through 180° and along path 107 which is parallel to exit path 103 and displaced from path 103 in the direction of the rotation axis of the prism 51. Preferably, roof prism 105 includes polarisation translation means 106, as described above, to allow the polarisation of the reflected radiation beam (e.g., on path 107) to be different than the polarisation of the beam entering the element for the first time (e.g., beam 101).

If the prism 51 is oriented such that the beam experiences the minimum delay, it exits the prism 51 at a position which is vertically shifted downwards from path 103 (not shown). The beam is still reflected through 180° by large roof prism 105 and the beam exits roof prism 105 along path 109 which is vertically shifted downwards from path 107.

Radiation following path 107 or 109 from roof prism 105 enters prism 51 and is internally reflected by the surfaces identified in relation to FIGS. 1A, 1B and 2 following a second radiation path, and exits the prism 51 along radiation path 111.

Regardless of the rotation position of the prism 51, the second radiation path is the first radiation path reversed and displaced along the rotation axis. Thus, radiation always exits the prism along exit path 111 which is parallel to path 103 and at a fixed displacement therefrom.

Radiation exiting prism along path 111 then impinges on lower roof prism 113 and is reflected through 180°. The beam exits lower roof prism 113 along path 115 which is parallel to and horizontally shifted from path 111.

Radiation following path 115 is then reflected back through rotating prism 51 along a third path which is parallel to the first and second paths. Radiation then exits the prism 51 along path 117. Path 117 is reflected through 180° by upper roof prism 105 such that the radiation exits roof prism 105 along path 118. Path 117 is the exit path for radiation experiencing the maximum delay due to prism 51.

Radiation following path 118 is then reflected back through rotating prism 51 along a fourth path which is parallel to the first, second and third paths. Radiation then exits the prism 51 along path 119. Path 119 is reflected through 180° by lower roof prism 113 such that the radiation exits roof prism 113 along path 121. Path 119 is the exit path for radiation regardless of the rotation position of the prism 51.

Radiation following path 121 is then reflected back through rotating prism 51 along a fifth path which is parallel to the first, second, third and fourth paths. Radiation then exits the prism 51 along path 123. Path 117 is reflected through 180° by upper roof prism 105 such that the radiation exits roof prism 105 along path 125. Path 123 is the exit path for radiation experiencing the maximum delay due to prism 51.

Radiation following path 125 is then reflected back through rotating prism 51 along a sixth and final path which is parallel to the first to fifth paths. Radiation then exits the prism 51 along path 127. Path 127 is the exit path for radiation regardless of the rotation position of the prism 51. Hence, the scanning delay line may be easily incorporated into any optical system since its beam exit path remains fixed regardless of the delay introduced by the oscillating prism 51.

Figure 6:
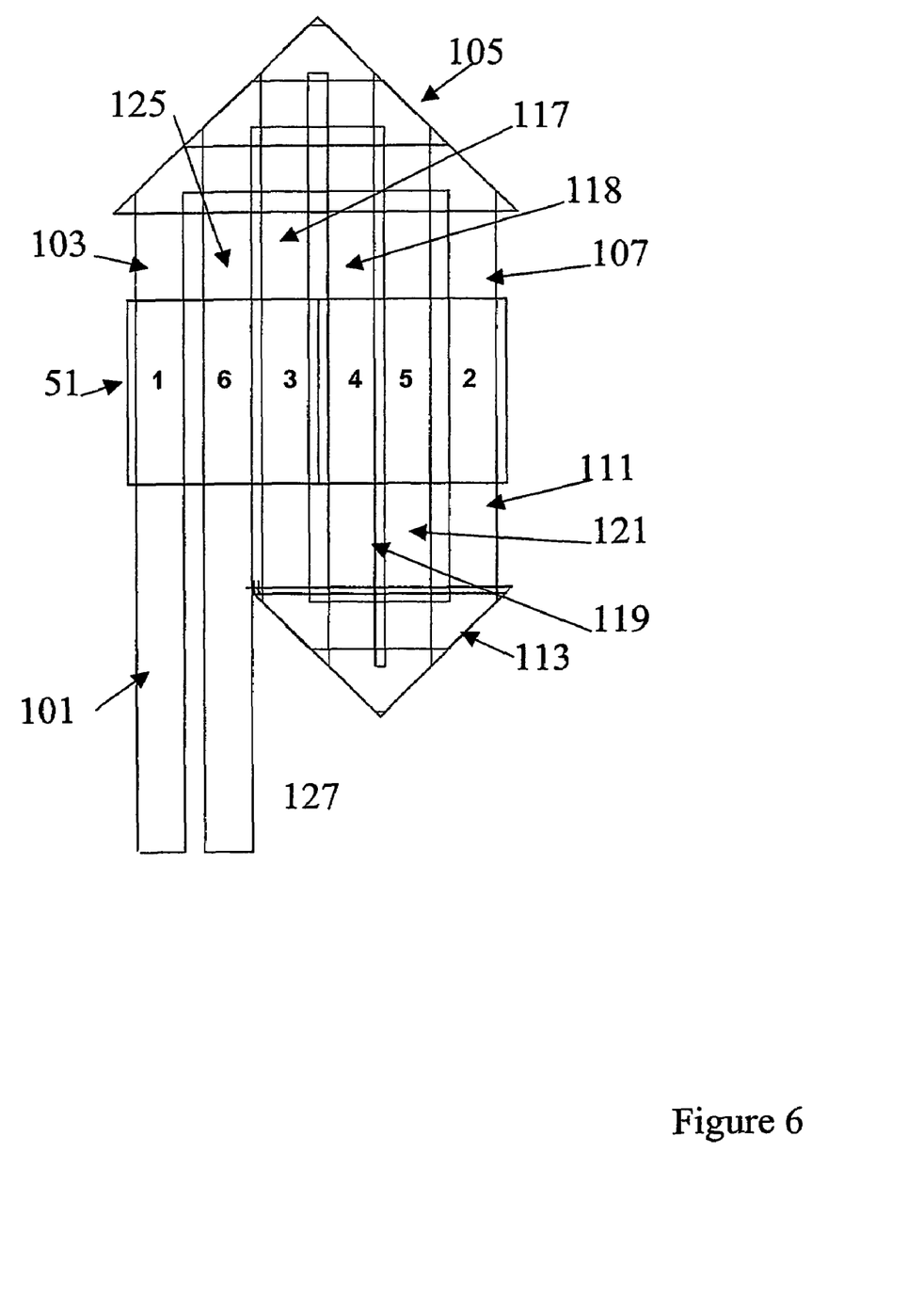
FIG. 6 is a schematic of the radiation paths through the prism of FIG. 5.

FIG. 6 is a schematic of the first to sixth radiation paths through prism 51. To avoid unnecessary repetition, like reference numerals will be used to denote like features.

The first and second radiation paths (paths 1 and 2) are seen to be at the furthest ends of prism 51. The third and fourth radiation paths (paths 3 and 4) are the innermost paths. The fifth path (path 5) is between the second and fourth paths and the sixth path (path 6) is between the first and third paths. This arrangement is chosen because the roof prisms are each symmetric. The lower roof prism 113 is provided offset from the upper prism 105 in order to achieve the described paths through the prism 51.

By multiply reflecting the radiation back through the prism 51, the delay introduced by the prism may be increased.

Figure 7:
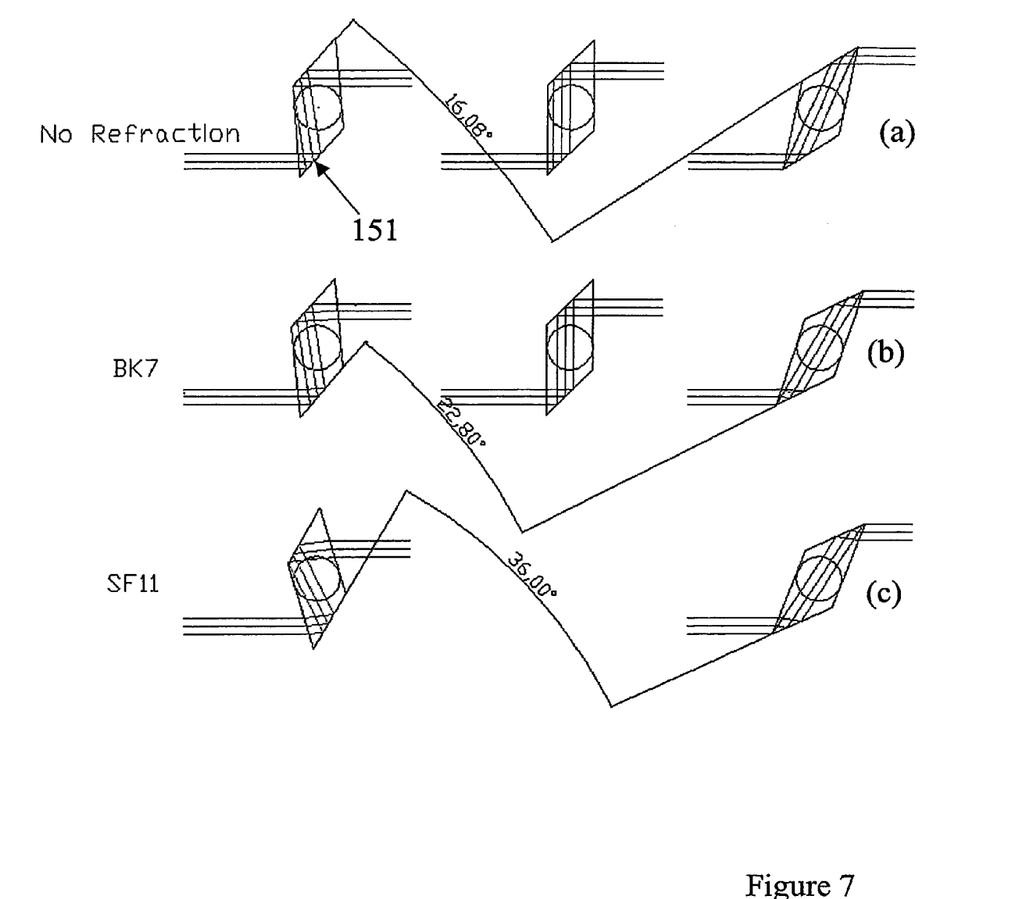
FIGS. 7a to 7c are schematics illustrating how the angle of rotation through which radiation is correctly reflected may be enhanced by increasing the refractive index of the material used to form the element.

FIGS. 7a to 7c schematically illustrate the effect of using a solid optic as the prism and fabricating the solid optic from a material with a high refractive index. FIG. 7a schematically illustrates the useable angle of through which the prism 151 may be rotated when the refractive index inside the prism matches the refractive index of the environment of the prism. This angle is seen to be 16.08° for the geometry of the prism of FIG. 7a. The useable angle is the angle through which the prism may be rotated and still correctly reflects and directs the radiation. A description of correct and incorrect reflection is given with respect to FIGS. 1 and 2.

FIG. 7b schematically illustrates the useable angle of through which the prism 151 may be rotated when the refractive index is of the prism is slightly higher than the refractive index of the environment of the prism. The useable angle in this case for the same geometry of FIG. 7a is 22.80°.

FIG. 7c schematically illustrates the useable angle of through which the prism 151 may be rotated when the refractive index is of the prism is slightly higher than the refractive index of the environment of the prism. The useable angle in this case for the same geometry of FIG. 7a is 36.80°.

Thus, by increasing the refractive index of the material of the solid optic, the prism may be rotated through a larger angle which still allows correct reflection of the radiation. Thus, the path length variation introduced by the prism may be substantially enhanced by increasing the refractive index of the prism.

Figure 8:
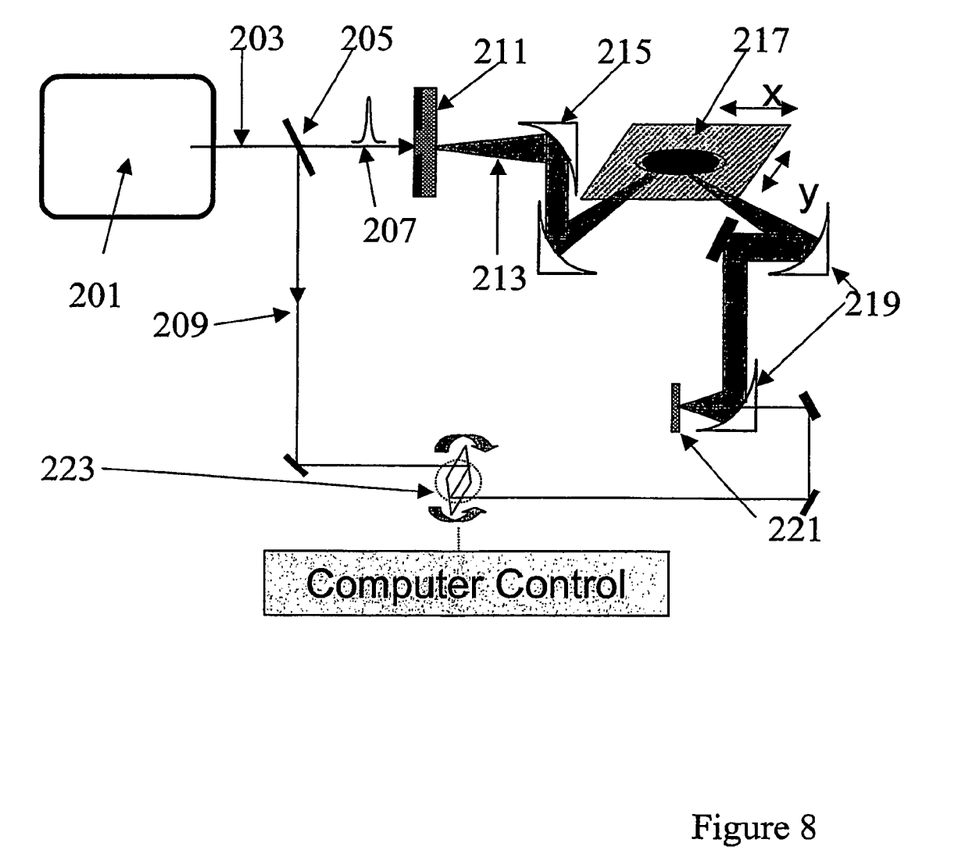
FIG. 8 is a schematic of an investigative system in accordance with a further embodiment of the present invention.

The delay element described with reference to FIGS. 1 to 7 is primarily intended for use in investigative systems and primarily those which operate using THz radiation. Such a system is schematically shown in FIG. 8.

Laser 201 outputs a beam of radiation 203, this is divided by beam splitter 205 into a pump beam 207 and a probe beam 209. The radiation emitted by laser 201 will typically be in the mid-infrared range. In order to produce THz radiation, the mid-infrared pump beam 207 impinges on THZ emitter 211. THz emitter 211 comprises a photoconductive substrate and two electrodes provided on said substrate. Terahertz beam 213 is emitted from emitter 211 and is guided via mirrors 215 onto sample 217. Sample 217 is provided on a motorised stage which allows it to move in the X and Y directions. The X and Y directions being orthogonal to one another such that a large area of the sample may be scanned. The reflected radiation is then directed via mirrors 219 onto detector 221.

In this type of imaging system, a probe beam 209 is also provided to the detectors 221. In order to determine the phase shifts introduced by sample 217, the phase of probe beam 209 is varied over a small range in order to continually vary the phase of the probe beam reaching detector 221. To achieve this, the pulse beam is passes through scanning delay line 223 which has been described with reference to FIGS. 1 to 7.

The invention claimed is:

1. An apparatus for varying the path length of a beam of radiation, the apparatus comprising:
    an element rotatably mounted about an axis, said element comprising two reflective surfaces in fixed relation to one another such that radiation is reflected between said reflective surfaces and out of the element; and
    driving means for rotatably oscillating said element back and forth about said axis, wherein said driving means comprises a galvanometer.

2. An apparatus according to claim 1, wherein said driving means is configured to vary the speed of the element during each oscillation such that the path length is varied linearly with time.

3. An apparatus according to claim 1, wherein said driving means is configured to oscillate said element through an angle of at most 40°.

4. An apparatus according to claim 1, wherein said element comprises a solid optic and said reflective surfaces are provided by surfaces of said optic.

5. An apparatus according to claim 4, wherein the said reflective surfaces are metallised.

6. An apparatus according to claim 4, wherein said solid optic is a rhomboid prism and said surfaces are two facing surfaces of said rhomboid.

7. An apparatus according to claim 4, wherein the solid optic comprises a material having a higher refractive index than 1.

8. An apparatus according to claim 7, wherein the solid optic has a refractive index of at least 1.2.

9. An apparatus according to claim 1, further comprising a reflecting member configured to reflect radiation exiting the element back into the element, the reflecting member being configured such that radiation reflected back into the element exits the element along a fixed final exit path regardless of the rotational position of the element.

10. An apparatus according to claim 9, wherein radiation which enters the element for a first time follows a first path and the reflecting member is configured to reflect radiation back into the element such that the radiation reflected by the reflecting member follows the first path in reverse.

11. An apparatus according to claim 10, wherein said reflecting member is provided with polarisation translation means.

12. An apparatus according to claim 9, wherein radiation which enters the element for a first time follows a first path and the reflecting member is configured to reflect radiation back into the element such that the reflected radiation follows a second path, said second path being said first path reversed and displaced along said rotation axis.

13. An apparatus according to claim 9, wherein said reflecting member is a first reflecting member and the apparatus further comprises a second reflecting member, said first and second reflecting members being configured such that radiation may be reflected back through said element at least four times.

14. A system for investigating a sample, the system comprising:
    an emitter for emitting radiation to irradiate said sample;
    a detector for detecting radiation reflected from or transmitted by said sample, radiation travelling from the emitter to the detector following a first path;
    means for supplying radiation along a second path to said detector and having a phase related to that of the radiation leaving the emitter, the system further comprising an apparatus according to claim 1, provided within either of the first or second paths.

15. A method for varying the path length of a beam of radiation, the method comprising:
    providing an element comprising two reflective surfaces in fixed relation to one another such that radiation is reflected between said reflective surfaces and out of the element;
    rotatably mounting said element about an axis; and
    rotatably oscillating said element back and forth about said axis using a galvanometer.

* * * * *